United States Patent
Logan et al.

(12) 
(10) Patent No.: US 6,392,074 B1
(45) Date of Patent: May 21, 2002

(54) METHOD FOR PREPARING SEBACIC ACID AND OCTANOL-2

(76) Inventors: Roger L. Logan, 20 Oxbow La., Newfoundland, NJ (US) 07435; Subhash V. Udeshi, 13AB Sett Minar 16A Peddar Road, Mumbai 400 026 (IN)

( * ) Notice: Subject to any disclaimer, the term of this patent is extended or adjusted under 35 U.S.C. 154(b) by 0 days.

(21) Appl. No.: 09/570,794

(22) Filed: May 12, 2000

(51) Int. Cl.$^7$ ............................................. C07C 51/00
(52) U.S. Cl. ...................................... 554/156; 554/157
(58) Field of Search ............................... 554/132, 156, 554/157

(56) References Cited

U.S. PATENT DOCUMENTS

| | | | |
|---|---|---|---|
| 2,674,608 A | * | 4/1954 | Dupont et al. ............... 260/406 |
| 5,952,517 A | * | 9/1999 | Ries et al. .................. 554/132 |

* cited by examiner

Primary Examiner—Deborah D. Carr
(74) Attorney, Agent, or Firm—Jean-Marc Zimmerman

(57) ABSTRACT

A process for producing a cleaved product from a ricinic compound by a high temperature reaction, achieved by combining an alkali in aqueous solution, a thinning agent, and a ricinic compound at a first temperature sufficient to distill off volatiles in the reaction mixture and then raising the temperature to a temperature sufficient to initiate a pyrolysis reaction and form a cleaved product from the ricinic compound, wherein the amount of thinning agent is in at a level sufficient to reduce the solidification of the mass during the reaction and foaming and increase the yield and purity of the products. The thinning agent is an isocarboxylic acid, an isoaldehyde or an isoalcohol containing from 5 to 13 carbon units. The thinning agent is relatively inexpensive, non-volatile and resistant to decomposition under the reaction conditions, easy to recover, and a non-foaming agent. The ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, ricinoleyl acid, a ricinoleyl acid amide, ricinoleyl alcohol, ricinoleyl alcohol. ester, an alkali ricinoleate or a mixture thereof The reaction mixture is acidified at the end of the reaction to allow for effective recovery of the thinning agent and the products. The invention also relates to the reaction mixture used in this cleavage reaction. The invention is useful in producing cleaved products of high yield and purity.

23 Claims, No Drawings

# METHOD FOR PREPARING SEBACIC ACID AND OCTANOL-2

FIELD OF INVENTION

The present invention relates to a process by which ricinic compounds such as castor oil or its major constituent ricinoleic acid can be converted into sebacic acid and octanol-2 under high temperature oxidative conditions. This reaction involves the addition of an alkali in aqueous solution in the presence of a thinning agent, which will change the fluidity of the solution allowing for improved yield and efficiency of the reaction and improved purity of the products. The thinning agent should be in amount sufficient to reduce foaming and solidification of the product, while improving the yield of the reaction.

BACKGROUND OF THE INVENTION

Sebacic acid is a valuable precursor for the production of nylon 6, 10. Octanol-2 is also a commercially useful chemical. The reaction to cleave castor oil in a strongly basic solution under heat to produce sebacic acid and octanol-2 is well known in the art. Addition of alkali salts at high temperatures will cause these reactants to solidify and cause foaming due to the production of soaps. This solidified reaction mixture is hard to stir by mechanical means. Various approaches have been taken to address the problem of viscous or solid soap solutions.

U.S. Pat. No. 2,674,608 to George DuPont has tried to solve the problem of excessive viscosity thickening in the cleavage reaction of castor oil by the addition of substantial amounts of phenolic compounds such as cresol and phenol. The formed alkali metal phenoxides have low volatility at 200–300° C. and remain in the reaction mass. After acidulation of the reaction mixture, to recover sebacic acid from its salt, it has been found phenol is also liberated. Phenol is soluble in water and will contaminate the sebacic acid. Foaming is also a problem with phenol present.

U.S. Pat. No. 5,952,517 to Reis and assigned to CasChem uses heat transfer fluids such as an aromatic oil, glycol oil, a petroleum oil, a fluorocarbon oil or silicone oil as a dilutent to allow for mechanical agitation of the reaction mixture in the castor oil cleavage reaction. These fluids are typically high boiling and very difficult to recycle. Their presence as a contaminant in the sebacic acid, which is hard to remove by distillation also makes these oils unsuitable for nylon manufacture, and other high quality uses.

Other carboxylic acids have also been suggested as thinning agents in this reaction such as oleic and linoleic acids (C18). In addition, six to ten carbon unit (C6 to C10) carboxylic acids such as carproic, caprylic and capric acid have been. examined by the inventors. None of these acids has been successfully used as a thinning agent. These normal acids melt from 5° C. to 31° C. and their corresponding alkali salts are solid under the reaction conditions for the cleavage of the ricinic compounds. This is contrasted with the isocarboxylic acids of this invention such as isodecanoic acid or isooctanoic acid which melt from −50° C. to −100° C. The corresponding alkali salts of the isocarboxylic acids melt at much lower temperatures than the salts of normal acids. Therefore they act as nonvolatile thinning agents in the reaction.

The ideal thinning agent for the production of sebacic acid should be inexpensive, non-volatile and meltable under the reaction conditions, easy to recover, resistant to decomposition under the reaction conditions, and a non-foaming agent. None of the thinning agents cited currently in the patent or open literature meet all of the criteria as outlined above.

It is the primary object of this invention to develop an inexpensive thinning agent for the oxidation and cleavage reaction of ricinic compounds, which will allow for the successful thinning of the reaction mixture so as to allow for effective mixing and diffusion of by-products thus leading to higher yields and improved purity of the resulting sebacic acid product.

Another object of this invention is to develop a thinning agent that is easy to recover. Another object. of the invention is to develop a thinning agent that is non-volatile and meltable under the actual reaction conditions. Another object of the invention is to identify a thinning agent that is also prevents foaming. Another object of the invention is to develop a thinning agent that is stable to the reaction conditions employed in the oxidation.

SUMMARY OF THE INVENTION

This invention is an improved process for producing an organic carboxylic acid such as sebacic acid and an aliphatic alcohol such as octanol-2 from a ricinic compound such as castor oil and its derivatives. The process involves combining together in a reaction mixture an alkali in aqueous solution, a ricinic compound and a thinning agent and raising the temperature of the mixture to a level that will initiate a pyrolysis reaction to form a cleaved product from the ricinic compound. The thinning agent is present in sufficient amount to reduce solidification and foaming, while increasing the overall yield of the reaction and allowing for hydrogen to be liberated from the reaction. The thinning agent is oxidatively and/or thermally stable. The thinning agent can be selected from a group of low melting aliphatic organic isocarboxylic acids containing 5 to 13 carbon units (C5 to C13), such as isononanoic acids, 2 ethyl hexanoic acid, isovaleric acids, isodecanoic acids, and isotridecanoic acids. Also included are aliphatic organic isoaldehydes and isoalcohols from C 5 to C13 units, since these readily oxidize to the corresponding acid.

In one embodiment the reaction mixture is agitated to allow for uniform dispersion of the reactants. In one preferred embodiment the temperature of the reaction is about 200 to 350° C. In another preferred embodiment the alkali is chosen from sodium hydroxide and potassium hydroxide. In another preferred embodiment the alkali has a pH greater than 9. Also cited in this disclosure is the reaction mixture for producing a cleaved product from a ricinic compound containing a thinning agent. In another embodiment, the process further includes adding an acid to the cleaved product in an amount sufficient to convert the cleaved product into a free acid.

In a preferred embodiment, the ricinic compound is castor oil, ricinoleate, a ricinic acid ester, a ricinoleic acid, a ricinoleic acid amide, a ricinoleic acid ester, a sulfonated ricinoleate, a ricinic ester, a ricinic alcohol, ricinoleyl alcohol, ricinoleyl alcohol ester, an alkali ricinoleate or a mixture thereof In a more preferred embodiment, the ricinic compound is glycerol tri-ricinoleate, a glyceryl tri (12-acetyl ricinoleate), glyceryl tri(12-hydroxystearate), glyceryl tri (12-acetoxystearate), methyl ricinoleate, ethyl ricinoleate, isoalcohol esters of ricinoleic acid e.g. 2-ethylhexanol ricinoleate, capryl ricinoleate, propylene glycol ricinoleate, or a mixture thereof

DETAILED DESCRIPTION OF THE INVENTION

Isocarboxylic acids have been found to reduce the solidification and foaming tendency of the reaction mixture upon high temperature caustic oxidative cleavage of ricinic compounds such as castor oil and its derivatives leading to improved yield and purity of the product. This allows for the preparation of cleaved products such as di-sodium sebacate and octanol-2.

A big advantage of the isocarboxylic acids is that they are non-volatile in salt form, but are easily recovered after acid treatment of the products. They are resistant to thermal decomposition during the course of the reaction. The have the dual purpose of thinning the reaction mixture and reducing foaming. The alkali salts of isocarboxylic acids from C5 to C13 are the preferred thinning agents. Corresponding isoalcohols and isoaldehydes of these acids can be used also since they will readily oxidize to salts of carboxylic acids under the conditions employed in this caustic high temperature oxidative reaction. Some foaming may be produced as the result of the extra oxidative step. The process can be run in either the batch or continuous mode.

It has been found that it is not necessary to use catalysts such as alkali metal nitrates as suggested in the prior art (see Reis, U.S. Pat. No. 5,952,517) to produce high yields of sebacic acid and octanol-2 in this instant invention. Specifically, reaction solutions are added to a reactor which contains a heater and agitator. The reactor has a vapor pipe connected to a condenser for the collection of volatile products such as octanol-2. Subsurface steam line is also supplied. The aqueous alkali solution is preferably preheated to a temperature of 200–210° C. To this reaction mixture an isocarboxylic acid (or the alcohol or aldehyde equivalent) and a ricinic compound are slowly added, preferably over a 1–4 hour period. A small amount of subsurface steam is added during the first few hours of reaction. Volatile products, such as octanol are distilled from the reactor at a suitable temperature with the addition of steam. The temperature is raised to 200–350° C. and maintained until hydrogen evolution has been completed. The distillate is recovered from the condensate receiver. The sodium salts from the reaction are diluted with water and acidulated with an acid such as sulfuric acid. The isocarboxylic acid thinning agent are recovered by vacuum distillation for reuse. Sebacic acid can be preferably extracted by hot water and crystallized to obtain the pure product.

Set forth below are exemplary examples of the present invention.

EXAMPLE 1: WITH 2-ETHYL HEXANOIC ACID AND CASTOR OIL

The reactor was supplied with a heater and agitator equipped with an ammeter. The agitator amperage had been previously calibrated to indicate viscosity during the reaction. The reactor had a vapor pipe connected to a condenser for octanol-2, and was provided with a sub-surface steam line. 1300 parts of 85% sodium hydroxide was added and pre-heated to 200–210° C. Then 1300 parts of castor oil and 550 parts of 2 ethyl hexanoic acid were slowly added over two hours. A small amount of steam was added sub-surface, during the first two hours of reaction. The ammeter on the reactor motor showed 1.04 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 450 parts of crude octanol-2 containing 6% octanone-2 were recovered. The sodium salts from the reaction were diluted with water and acidulated with sulfuric acid. 525 parts of 2 ethyl hexanoic acid were recovered by vacuum distillation for reuse. Sebacic acid was extracted with hot water and 555 parts were crystallized from the water solution.

EXAMPLE 2: WITH 2-ETHYL HEXANOIC ACID AND RICINOLEIC ACID

The same reactor arrangement was used for this experiment as was used in example 1. 1300 parts of 85% sodium hydroxide and then preheated to 200–210° C. Then 1300 parts ricinoleic acid and 700 parts of 2 ethyl hexanoic acid were slowly added over two hours. A small amount of steam was added sub-surface, during the first two hours of reaction. The ammeter on the reactor motor showed 1.10 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 315° C. and held at this temperature until hydrogen evolution had stopped. 450 parts of crude octanol-2 containing 5% octanone-2 were recovered. The sodium salts from the reaction were diluted with water and acidulated with sulfuric acid. 650 parts of 2 -ethyl hexanoic acid were recovered by vacuum distillation for reuse. Sebacic acid was extracted with hot water and 570 parts were crystallized from the water solution.

EXAMPLE 3: WITH 2-ETHYL HEXANOIC ACID AND METHYL RICINOLOEATE

The same reactor arrangement was used for this experiment as was used in example 1. 1300 parts of 85% sodium hydroxide and then preheated to 200–210° C. Then 1300 parts ricinoleic acid and 700 parts of 2-ethyl hexanoic acid were slowly added over two hours. A small amount of steam was added sub-surface, during the first two hours of reaction. The ammeter on the reactor motor showed 1.10 amperes. Samples taken during the first two hours of reactions at the point of maximum viscosity could be observed as a flowable liquid, but slightly more viscous than example 1 where castor oil was used as the feed.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 445 parts of crude octanol-2 containing 5% octanone-2 were recovered. The sodium salts from the reaction were diluted with water and acidulated from sulfuric acid. 655 parts of 2-ethyl hexanoic acid were recovered by vacuum distillation for reuse. Sebacic acid was extracted with hot water and 550 parts were crystallized from the water solution.

EXAMPLE 4: WITH 2-ETHYL HEXANOIC ACID, CASTOR OIL, AND SODIUM AND POTASSIUM HYDROXIDE

The same reactor arrangement was used for this experiment as was used in example 1. 1000 parts of 85% sodium hydroxide and 420 parts of 85% potassium hydroxide was added to the reactor and then preheated to 200–210° C. Then 1300 parts castor oil and 540 parts of 2-ethyl hexanoic acid were slowly added over two hours. A small amount of steam was added sub-surface, during the first two hours of reaction. The ammeter on the reactor motor showed 0.95 amperes. Samples taken during the first two hours of reactions at the point of maximum viscosity could be observed as a soft flowable liquid.

Octanol-2 was distilled from the reactor at 200–210° C. with the addition of steam. After two hours at 210° C., the octanol-2 evolution was almost complete. The temperature was raised to 330° C. and held at this temperature until hydrogen evolution had stopped. 455 parts of crude octanol-2 containing 5% octanone-2 were recovered. The sodium salts and potassium salts from the reaction were diluted with water and acidulated with sulfuric acid. 515 parts of 2-ethyl hexanoic. acid were recovered by vacuum distillation for reuse. Sebacic acid was extracted with hot water and 560 parts were crystallized from the water solution.

EXAMPLE 5: CONTROL WITH CASTOR OIL, BUT WITH NO THINNING AGENT

The same reactor arrangement was used for this experiment as was used in example 1. 1300 parts of 85% sodium hydroxide was added to the reactor and then preheated to 200–210° C. Then 1300 parts castor oil were slowly added over two hours. A small amount of steam was added sub-surface, during the first two hours of reaction. The ammeter on the reactor motor showed 2.5 amperes. The agitator stopped and could not be restarted. Samples taken during the first two hours of reactions at the. point of maximum viscosity could be observed as a solid mass.

Octanol-2 was distilled from the reactor at 210–220C with the addition of steam. After 2 ½ hours at 210° C., the octanol-2 evolution was almost complete. The temperature was raised to 300° C. and held at this temperature until hydrogen evolution had stopped. Some foaming was observed. Only 275 parts of crude octanol-2 containing 10% octanone-2 were recovered. The sodium salts from the reaction were diluted with water and acidulated with sulfuric acid. Sebacic acid was extracted with hot water and 350 parts were crystallized from the water solution.

EXAMPLE 6: WITH ISONONANOIC ACID AND CASTOR OIL

The same reactor arrangement was used for this experiment as was used in example 1. 1300 parts of 85% sodium hydroxide was added to the reactor and then preheated to 200–210° C. Then 1300 parts castor oil and 750 parts of isononanoic acid were slowly added over two hours. A small amount of steam was added sub-surface, during the first two hours of reaction. The ammeter on the reactor motor showed 1. 11 amperes. Samples taken during the first two hours of reactions at the point of maximum viscosity could be observed as a flowable liquid, but somewhat more viscous than example 1 where castor oil was used as the feed.

Octanol-2 was distilled from the reactor at 200–210° C. with the addition of steam. After two hours at 210° C., the octanol-2 evolution was almost complete. The temperature was raised to 320° C. and held at this temperature until hydrogen evolution had stopped. 475 parts of crude octanol-2 containing 6% octanone-2 were recovered. The sodium salts from the reaction were diluted with water and acidulated with sulfuric acid. 700 parts of isononanoic were recovered by vacuum distillation for reuse. Sebacic acid was extracted with hot water and 550 parts were crystallized from the water solution.

EXAMPLE 7: WITH 2-ETHYL HEXYL ALDEHYDE AND CASTOR OIL

The same reactor arrangement was used for this experiment as was used in example 1. 1300 parts of 85% sodium hydroxide was added to the reactor and then preheated to 200–210° C. Then 1300 palts castor oil were slowly added over two hours. 600 parts of 2-ethyl hexyl aldehyde (2-ethyl hexanal) was carefully added separate from the castor oil. 2-ethyl hexanal is known to oxidize to 2-ethyl hexanoic acid under these test conditions. A small amount of steam was added sub-surface, during the first two hours of reaction. The ammeter on the reactor motor showed 1.30 amperes. Samples taken during the first two hours of reactions at the point of maximum viscosity could be observed as a flowable liquid, but somewhat more viscous than example 1 where 2-ethyl hexanoic acid was used as the thinning agent and castor oil was used as the feed.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 400 parts of crude octanol-2 containing 6% octanone-2 were recovered. The sodium salts from the reaction were diluted with water and acidulated with sulfuric acid. 500 parts of 2 ethyl hexanoic acid were recovered by vacuum distillation for reuse. Sebacic acid was extracted with hot water and 500 parts were crystallized from the water solution. There was some evidence in the by-product recovery that some of the 2-ethyl hexanal polymerized through an aldol condensation.

EXAMPLE 8: WITH ISOALDEHYDES, ISOALCOHOLS AND ISOCARBOXYLIC ACIDS AND CASTOR OIL

The same reactor arrangement was used for this experiment as was used in example 1. 1300 parts of 85% sodium hydroxide was added to the reactor and then preheated to 200–210° C. Then 1300 parts castor oil were slowly added over two hours. 600 parts of a mixture of C-13, 30% isoaldehydes, 25% isoalcohols and 45% isocarboxylic acid mixture was carefully added separate from the castor oil. This mixture was predominately tetra methyl 1-nonanol, tetra methyl 1-nonanal, and tetra methyl 1-nonanoic acid. The aldehydes and alcohols are known to oxidize to acids under these test conditions. A small amount of steam was added sub-surface, during the first two hours of reaction. The ammeter on the reactor motor showed 1.0 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 445 parts of crude octanol-2 containing 6% octanone-2 were recovered. The sodium salts from the reaction were diluted with water and acidulated with sulfuric acid. 500 parts of mainly isotridecanoic acids were recovered by vacuum distillation for reuse. Sebacic acid was extracted with hot water and 550 parts were crystallized from the water solution.

EXAMPLE 9: WITH ISODECANOIC ACID AND CASTOR OIL

The same reactor arrangement was used for this experiment as was used in example 1. 1300 parts of 85% sodium hydroxide was added to the reactor and then preheated to 200–210° C. Then 1300 parts castor oil and 800 parts of isodecanoic acids were slowly added over two hours. A small amount of steam was added sub-surface, during the first two hours of reaction. The ammeter on the reactor motor showed 0.95 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 330° C. and held at this temperature until hydrogen evolution had stopped. 455 parts of crude octanol-2 containing 5% octanone-2 were recovered. The sodium salts from the reaction were diluted with water and acidulated with sulfuric acid. 750 parts of isodecanoic acid were recovered by vacuum distillation for reuse. Sebacic acid was extracted with hot water and 560 parts were crystallized from the water solution.

EXAMPLE 10: WITH ISOVALERIC ACID AND CASTOR OIL

The same reactor arrangement was used for this experiment as was used in example 1. 1300 parts of 85% sodium hydroxide was added to the reactor and then preheated to 200–210° C. Then 1300 parts castor oil and 600 parts of isovaleric acid were slowly added over two hours. Isovaleric acid consisted mainly of 2 and 3 methyl butyric acid. A small amount of steam was added sub-surface, during the first two hours of reaction. The ammeter on the reactor motor showed 1.00 amperes. Samples taken during the first two hours of reactions at the point of maximum viscosity could be observed as a very flowable liquid.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 460 parts of crude octanol-2 containing 5% octanone-2 were recovered. The sodium salts from the reaction were diluted with water and acidulated with sulfuric acid. 500 parts of isovaleric acid were recovered by vacuum distillation for reuse. Sebacic acid was extracted with hot water and 530 parts were crystallized from the water solution.

EXAMPLE 11: with isooctanoic acid and ricinoleic acid

The same reactor arrangement was used for this experiment as was used in example 1. 1300 parts of 85% sodium hydroxide was added to the reactor and then preheated to 200–210° C. Then 1300 parts ricinoleic acid and 675 parts of isooctanoic acid were slowly added over two hours. A small amount of steam was added sub-surface, during the first two hours of reaction. The ammeter on the reactor motor showed 0.95 amperes. Samples taken during the first two hours of reactions at the point of maximum viscosity could be observed as a flowable liquid, somewhat more viscous than when castor oil was used as a feed.

Octanol-2 was distilled from the reactor at 200–210° C. with the addition of steam. After two hours at 210° C., the octanol-2 evolution was almost complete. The temperature was raised to 310° C. and held at this temperature until hydrogen evolution had stopped. 470 parts of crude octanol-2 containing 5% octanone-2 were recovered. The sodium salts from the reaction were diluted with water and acidulated with sulfuric acid. 625 parts of isooctanoic acid were recovered by vacuum distillation for reuse. Sebacic acid was extracted with hot water and 580 parts were crystallized from the water solution.

EXAMPLE 12: WITH 2-METHYL UNDECANAL AND CASTOR OIL

The same reactor arrangement was used for this experiment as was used in example 1. 1300 parts of 85% sodium hydroxide was added to the reactor and then preheated to 200–210° C. Then 1300 parts castor oil were slowly added over two hours. 600 parts of 2-methyl undecanal was carefully added separate from the castor oil. 2-methyl undecanal is known to oxidize to 2-methyl undecanoic acid under these test conditions. A small amount of steam was added sub-surface, during the first two hours of reaction. The ammeter on the reactor motor showed 1.2 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 300° C. and held at this temperature until hydrogen evolution had stopped. 400 parts of crude octanol-2 containing 6% octanone-2 were recovered. The sodium salts from the reaction were diluted with water and acidulated with sulfuric acid. 440 parts of 2-methyl undecanoic acid were recovered by vacuum distillation for reuse. Sebacic acid was extracted with hot water and 475 parts were crystallized from the water solution. There was some evidence in the by-product recovery that some of the 2-methyl undecanal polymerized through an aldol condensation.

EXAMPLE 13: WITH TRIDECYL ALCOHOL AND CASTOR OIL

The same reactor arrangement was used for this experiment as was used in example 1. 1300 parts of 85% sodium hydroxide was added to the reactor and then preheated to 200–210° C. Then 1300 parts castor oil were slowly added over two hours. 650 parts tridecyl alcohol which was predominately tetra methyl 1-nonanol was carefully added with the castor oil. Tridecyl alcohol is known to oxidize to tridecanoic acid under these test conditions. A small amount of steam was added sub-surface, during the first two hours of reaction. The ammeter on the reactor motor showed 0.90 amperes. Samples taken during the first two hours of reactions at the point of maximum viscosity could be observed as a flowable liquid.

Octanol-2 was distilled from the reactor at 200–210° C. with the addition of steam. After two hours at 210° C., the octanol-2 evolution was almost complete. The temperature was raised to 350° C. and held at this temperature until hydrogen evolution had stopped. 445 parts of crude octanol-2 containing 6% octanone-2 and 25% tridecyl alcohol were recovered. A recovered mixture of alcohols had a composition of 445 parts of crude octanol-2, 5% octanone-2, and 150 parts of tridecyl alcohol. The octanol-2 and octanone-2, boiling at 180° C. and the tridecanol boiling at 253–263° C. were separated by fractional distillation and the recovered tridecanol was reused. The remaining 400 parts of tridecanoic acid which was oxidized in the reaction mixture to the sodium salts of tridecanoic acid. The sodium salts from the reaction were diluted with water and acidulated with sulfuric acid. 400 parts of mainly tridecanoic acid were recovered by vacuum distillation for reuse. Sebacic acid was extracted with hot water and 550 parts were crystallized from the water solution.

Numerous modifications to and alternative embodiments of the present invention will be apparent to those skilled in the art in view of the foregoing description. Accordingly, this description is to be construed as illustrative only and is for the purpose of teaching those skilled in the art the best mode of carrying out the invention. Details of the structure may be. varied substantially without departing from the spirit of the invention and the exclusive use of all the modifications which come within the scope of the appended claims is reserved.

We claim:

1. A method for producing a cleaved product from a ricinic compound by a high temperature concentrated alkali reaction, comprising the steps of:
    combining an alkali in aqueous solution, a thinning agent selected from the group consisting of isocarboxylic acid, isoaldehyde and isoalcohol, and a ricinic compound at a first temperature sufficient to distill off volatiles in the reaction mixture;
    and raising the temperature to a temperature sufficient to initiate a pyrolysis reaction and form a cleaved product from the ricinic compound,
    wherein the amount of thinning agent is present at an effective amount sufficient to reduce the solidification of the mass during the reaction and foaming.

2. The method according to claim 1, wherein the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, ricinoleyl acid, a ricinoleyl acid amide, ricinoleyl alcohol, ricinoleyl alcohol ester, an alkali ricinoleate or a mixture thereof.

3. The method according to claim 1, further comprising the step of adding an acid to the reacted mixture in an amount sufficient to react all of the cleaved product into a free acid to allow for separating and collecting of the final products.

4. The method according to claim 1, further comprising the step of preheating the aqueous alkali solution prior to adding the other reactants.

5. The method according to claim 1, wherein the reaction temperature is raised to a point between 200 to 350° C.

6. The method according to claim 1, wherein the thinning agent is oxidatively stable.

7. The method according to claim 1, wherein the thinning agent is thermally stable.

8. The method according to claim 1, wherein the thinning agent is an aliphatic organic isocarboxylic acid, isoalcohol and isoaldehyde of 5 to 13 carbon units chain length or a mixture thereof.

9. The method according to claim 8, wherein the thinning agent isocarboxylic acid is isononanoic acid, 2 ethyl hexanoic acid, isovaleric acid, isodecanoic acid, and tridecanoic acid.

10. The method according to claim 8, wherein the thinning agent isoalcohol is tridecyl alcohol.

11. The method according to claim 8, wherein the thinning agent isoaldhehyde is undecanal, 2-ethyl hexanal, isovaleric aldehyde, and tetra methyl 1-nonanal.

12. The method according to claim 1, wherein the thinning agent reduces foaming during the cleavage reaction.

13. The method according to claim 1, wherein the alkali has a pH greater than 9.

14. The method according to claim 1, wherein the alkali comprises sodium hydroxide.

15. The method according to claim 1, wherein the alkali comprises potassium hydroxide.

16. The method according to claim 3, wherein the free acid is sebacic acid.

17. The method according to claim 1, wherein the reaction mixture is mechanically agitated.

18. The method according to claim 2, wherein the ricinic compound is glycerol tri-ricinoleate, a glyceryl tri (12-acetyl ricinoleate), glyceryl tri(12-hydroxystearate), glyceryl tri (12-acetoxystearate), turkey red oil, methylated ricinoleate, methyl ricinoleate, capryl ricinoleate, propylene glycol ricinoleate, or a mixture thereof.

19. A reaction mixture for producing a cleaved product from a ricinic compound by high temperature oxidation comprising:
    a ricinic compound;
    an alkali in aqueous solution;
    a thinning agent selected from the group consisting of isocarboxylic acid, isoaldehyde and isoalcohol and present in an effective amount sufficient to reduce solidification and foaming in the reaction mixture to allow for increased yield and purity of the products.

20. The reaction mixture according to claim 19, wherein the thinning agent is an aliphatic organic isocarboxylic acid, isoalcohol and isoaldehyde of 5 to 13 carbon units chain length or a mixture thereof.

21. The reaction mixture according to claim 19, wherein the ricinic compound is castor oil, a ricinoleate, a ricinic acid ester, a ricinoleic acid, a ricinoleic acid amide, a ricinoleic acid ester, a sulfonated ricinoleate, a ricinic ester, a ricinic alcohol, ricinoleyl acid, a ricinoleyl acid amide, riccinoleyl alcohol, ricinoleyl alcohol ester, an alkali ricinoleate or a mixture thereof.

22. The reaction mixture according to claim 19, wherein the thinning agent isocarboxylic acid is isononanoic acid, 2 ethyl hexanoic acid, isovaleric acid, isodecanoic acid, and tridecanoic acid.

23. The method according to claim 1, wherein the alkali is selected from the group consisting of sodium hydroxide and potassium hydroxide.

* * * * *